United States Patent [19]
Hofmann

[11] Patent Number: 6,132,419
[45] Date of Patent: Oct. 17, 2000

[54] ELECTROPORETIC GENE AND DRUG THERAPY

[75] Inventor: Gunter A. Hofmann, San Diego, Calif.

[73] Assignee: Genetronics, Inc., San Diego, Calif.

[21] Appl. No.: 08/328,895

[22] Filed: Oct. 25, 1994

Related U.S. Application Data

[63] Continuation-in-part of application No. 08/041,510, Apr. 11, 1993, abandoned, which is a continuation-in-part of application No. 07/887,315, May 22, 1992, abandoned.

[51] Int. Cl.[7] .............................. A61K 9/22; A61N 1/30; A61N 1/18; A61M 31/00
[52] U.S. Cl. .................................. 604/890.1; 604/891.1; 604/20; 604/500; 604/507; 607/3; 607/68; 607/72; 607/74; 607/115; 435/173.6; 204/451; 204/601
[58] Field of Search .............................. 600/1, 2, 12, 13, 600/14, 15; 604/890.1, 891.1, 892.1, 20, 21, 49, 52, 54; 435/172.2, 173.6, 287, 289; 204/180.1, 299 R; 938/52; 128/639, 642, 644; 607/1–3, 65, 72, 74, 98–101, 113, 115–117, 120–121, 144–145, 154–156

[56] References Cited

U.S. PATENT DOCUMENTS

| | | | |
|---|---|---|---|
| 2,320,462 | 6/1943 | Nawells | 607/148 |
| 3,978,864 | 9/1976 | Smith et al. | 604/155 |
| 4,440,178 | 4/1984 | Bussard et al. | 607/121 |
| 4,639,244 | 1/1987 | Rizk et al. | 604/891.1 |
| 4,690,130 | 9/1987 | Mirell | 600/2 |
| 4,801,459 | 1/1989 | Liburdy | 600/2 |
| 4,842,598 | 6/1989 | Tran | 604/891.1 |
| 4,906,576 | 3/1990 | Marshall, III | 435/287 |
| 4,936,317 | 6/1990 | MacGregor | 607/120 |
| 4,970,154 | 11/1990 | Chang | 435/172.2 |
| 5,016,615 | 5/1991 | Driller et al. | 604/891.1 |
| 5,019,034 | 5/1991 | Weaver et al. | 604/890.1 |
| 5,042,975 | 8/1991 | Chien et al. | 604/20 |
| 5,087,243 | 2/1992 | Avitall | 607/120 |
| 5,098,843 | 3/1992 | Calvin . | |
| 5,128,257 | 7/1992 | Baer . | |
| 5,183,456 | 2/1993 | Liboff et al. | 600/13 |
| 5,224,922 | 7/1993 | Kurtz | 600/13 |
| 5,236,413 | 8/1993 | Feiring | 607/116 |
| 5,246,437 | 9/1993 | Abela | 604/21 |
| 5,273,525 | 12/1993 | Hofmann | 604/21 |

(List continued on next page.)

FOREIGN PATENT DOCUMENTS

| | | | |
|---|---|---|---|
| 686287 | 3/1965 | Italy | 607/145 |
| 0624640 | 9/1978 | U.S.S.R. | 604/20 |
| 8910690 | 11/1989 | WIPO | 604/20 |

OTHER PUBLICATIONS

Engineering Circuit Analysis, 3rd Ed. pp. 136–137, 526–529.

Modern Dictionary of Electronics, p. 156, 242.

*Primary Examiner*—John G. Weiss
*Assistant Examiner*—K. M. Reichle
*Attorney, Agent, or Firm*—Baker & Maxham

[57] ABSTRACT

A method and apparatus are provided for introducing molecules such as genes and pharmaceutical compounds into living blood cells of a patient for therapeutic purposes. A device is placed into contact with the body of the patient for generating an electric field at a preselected location within a selected blood vessel. Preselected molecules are infused into the selected blood vessel. Simultaneously an electric signal is applied to the applied device to repeatedly subject a quantity of blood flowing within the selected blood vessel past the preselected location to electric fields of a predetermined amplitude and duration. The parameters of the electric fields are precisely controlled in order to make the walls of preselected cells in the blood transiently permeable to permit the molecules to enter said preselected cells without killing said cells. The device can include either an induction coil that is placed into contact with the body over a blood vessel, or alternatively, an induction coil that surrounds the blood vessel. The electric signal is supplied by a power pack and the preselected molecules are infused with a supply pump.

21 Claims, 3 Drawing Sheets

U.S. PATENT DOCUMENTS

| | | | |
|---|---|---|---|
| 5,286,254 | 2/1994 | Shapland et al. | 604/21 |
| 5,290,409 | 3/1994 | Liboff et al. | 606/13 |
| 5,304,120 | 4/1994 | Crandell et al. | 604/52 |
| 5,318,514 | 6/1994 | Hofmann | 604/20 |
| 5,389,069 | 2/1995 | Weaver | 604/21 |
| 5,419,763 | 5/1995 | Hildebrand | 604/54 |
| 5,439,440 | 8/1995 | Hofmann | 604/20 |
| 5,501,662 | 3/1996 | Hofmann | 604/20 |

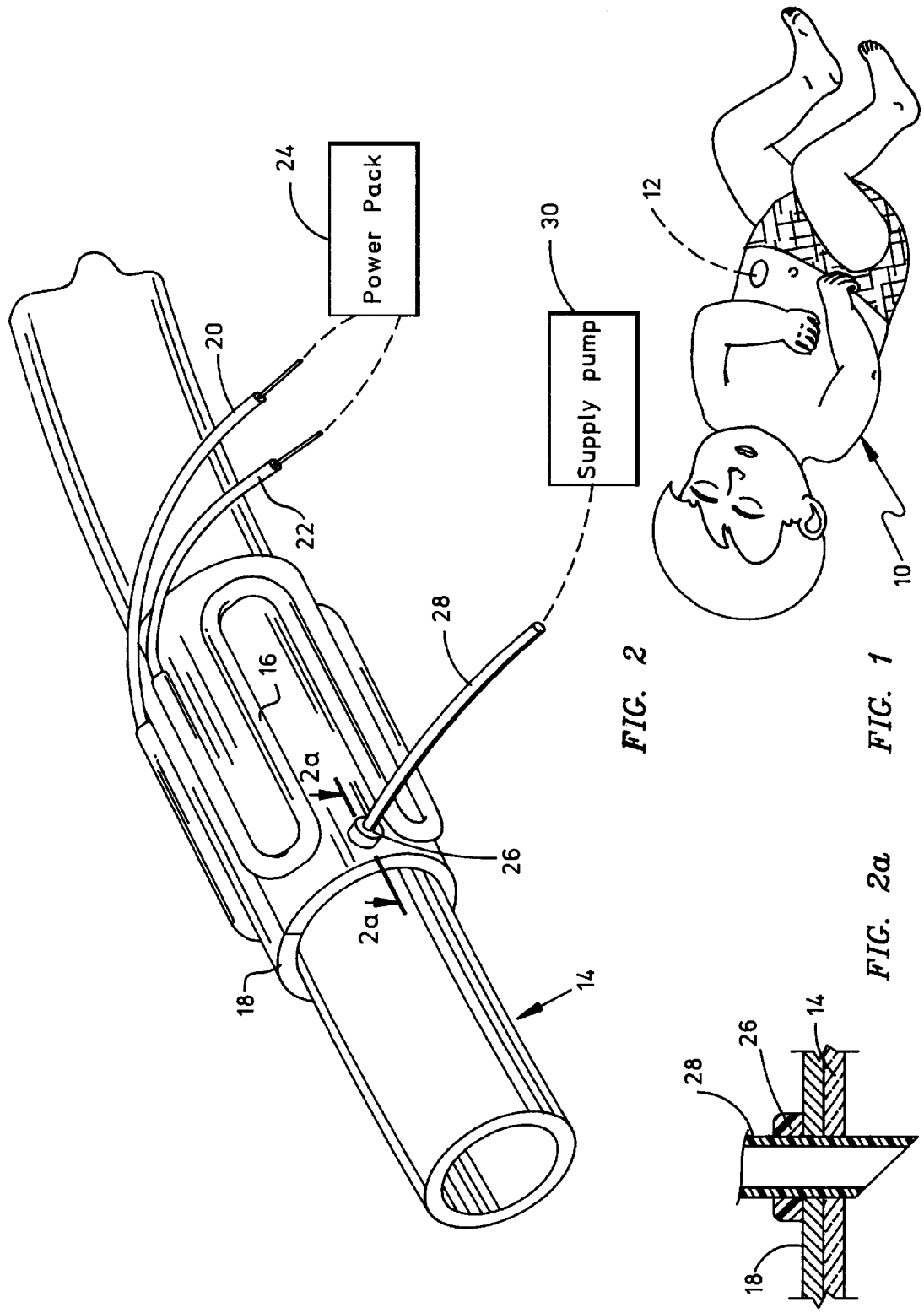

ELECTROPORETIC GENE AND DRUG THERAPY

The present application is a continuation-in-part of U.S. patent application Ser. No. 08/041,510 filed Apr. 1, 1993, which was a Continuation-in-part of U.S. patent application Ser. No. 07/887,315 filed May 22, 1992, entitled "IMPLANTABLE ELECTROPORATION METHOD AND APPARATUS FOR DRUG AND GENE DELIVERY", now both abandoned.

BACKGROUND OF THE INVENTION

The present invention relates to the treatment of ailments in humans and other mammals, and more particularly, to an apparatus and method for in vivo delivering of pharmaceutical compounds and genes into live cells of a patient.

It has long been known that it would be desirable to target certain cells within the body with specific pharmaceutical compounds. For example, in the treatment of certain types of cancer with chemotherapy it is necessary to use a high enough dose of a drug to kill the cancer cells without killing an unacceptably high number of normal cells. If the chemotherapy drug could be inserted directly inside the cancer cells, this objective could be achieved. However, some of the best anti-cancer drugs, for example, bleomycin, normally cannot penetrate the membranes of certain cancer cells.

Similarly, certain diseases could be treated by introducing desired genes into the specific cells of the patient. At present, most gene therapy experiments have utilized retroviruses as the carrier of the gene into the cells. When a retrovirus enters a target cell, it integrates essentially randomly in the genome and thus has the potential for introducing mutational damage by the mere fact of its insertion. If the virus integrates adjacent to an oncogeny, malignant transformation of the target cell can result.

The above identified grandparent application discloses an electroporation method and apparatus for the in vivo introduction of drugs and genes into blood cells with implanted electrodes and induction coils. Electroporation is a convenient purely physical method for introducing drugs and genes into living cells. It is known that genes and other molecules such as pharmaceutical compounds can be incorporated into live cells through a process known as electroporation. In the typical experiment, the genes or other molecules are mixed with the live cells in a buffer medium in a chamber with two electrodes. A voltage pulse is applied between the electrodes to create the electric field. The cell membranes are transiently made porous and the genes or molecules enter the cells. There they can modify the genome of the cell. Examples of the prior art are: U.S. Pat. No. 4,970,154 of Chang, U.S. Pat. No. 5,098,843 of Calvin and U.S. Pat. No. 5,128,257 of Baer. This direct contact method is not easily adapted to a live body situation which would require the implantation of the electrodes.

The incorporation of drugs into red blood cells via electroporation as well as the incorporation of genes into white blood cells via electroporation have both been demonstrated. The selective incorporation of genes into white blood cells in whole blood via electroporation has also been demonstrated. The electroporation of cells in a flow-through system utilizing a venturi in a static field has been proposed by Calvin in U.S. Pat. No. 5,098,843.

Recent methods of gene therapy have used the procedure wherein a substantial amount (e.g. 10%) of a patient's blood is withdrawn and the red and white blood cells are separated over a lengthy time period (e.g. four hours). The red blood cells are then re-infused. A new gene is inserted into the separated white blood cells utilizing a retrovirus. The growth of the white cells is then stimulated before they are re-infused into the patient. The procedure must be repeated every few months and the costs can reach $100,000.00 annually.

It would be desirable to eliminate the need for separating the white cells from the red blood cells. This in turn would eliminate the need to withdraw and re-infuse a portion of the patient's blood. This would make it more convenient and less expensive to perform gene therapy on living patients by genetically modifying their lymphocytes. It would also make it more convenient and less expense to deliver drugs to selected tissues and organs of a living human body by encapsulating them into red blood cells. It would also be desirable to eliminate the need to utilize retroviruses which can result in malignant transformation of the target cells.

Heretofore, an apparatus and method have not been provided to permit electroporation mediated, in vivo, intracellular drug and gene delivery through the blood vessels of a living patient. It would be desirable to provide such an apparatus and method because it would permit gene therapy of living patients by genetically modifying their lymphocytes. Such an apparatus and method would also be beneficial in providing a means for delivering drugs to selected tissues and organs of a living human body by encapsulating them into red blood cells. In general, such an apparatus and method would be advantageous in providing a means of delivery of antibodies, proteins, or other molecules into the red or white blood cells of a living patient.

It would also be desirable to have a method and apparatus to enable electroporation of selected blood cells without the implanting of electrodes within the body.

SUMMARY OF THE INVENTION

Accordingly, it is the primary object of the present invention to provide an improved method of electroporation mediated, in vivo, intracellular drug and gene delivery for a living patient.

It is another principal object of the present invention to provide an apparatus for electroporation mediated, in vivo, intracellular drug and gene delivery without invasion of the body.

In accordance with a primary aspect of the present invention, a coil is applied to the body of the patient for generating an electric field at a preselected location within a selected area or portion of tissue, preselected molecules are infused into the selected tissue, simultaneously an electric signal is applied to the applied coil to repeatedly subject the tissue to electric fields of a predetermined amplitude and duration. The parameters of the electric fields are precisely controlled in order to make the walls of preselected cells in the tissue transiently permeable to permit the molecules to enter said preselected cells without killing said cells. The device can include either one or more induction coils placed over the tissue, or alternatively, an induction coil that surrounds a limb or portion of the body containing the tissue. The electric signal is supplied to a power pack and the preselected molecules are infused with a supply pump.

BRIEF DESCRIPTION OF THE DRAWINGS

FIG. 1 illustrates a patient with a device applied to his body for effecting in vivo electroporation of molecules into a selected area or portion of the patient's body in accordance with the present invention.

FIG. 2 is an enlarged perspective view of an alternative embodiment of the apparatus for effecting in vivo electroporation of molecules into a blood vessel.

FIG. 2a is a section view taken on line 2a—2a of FIG. 2.

DESCRIPTION OF THE PREFERRED EMBODIMENTS

Figure 3:
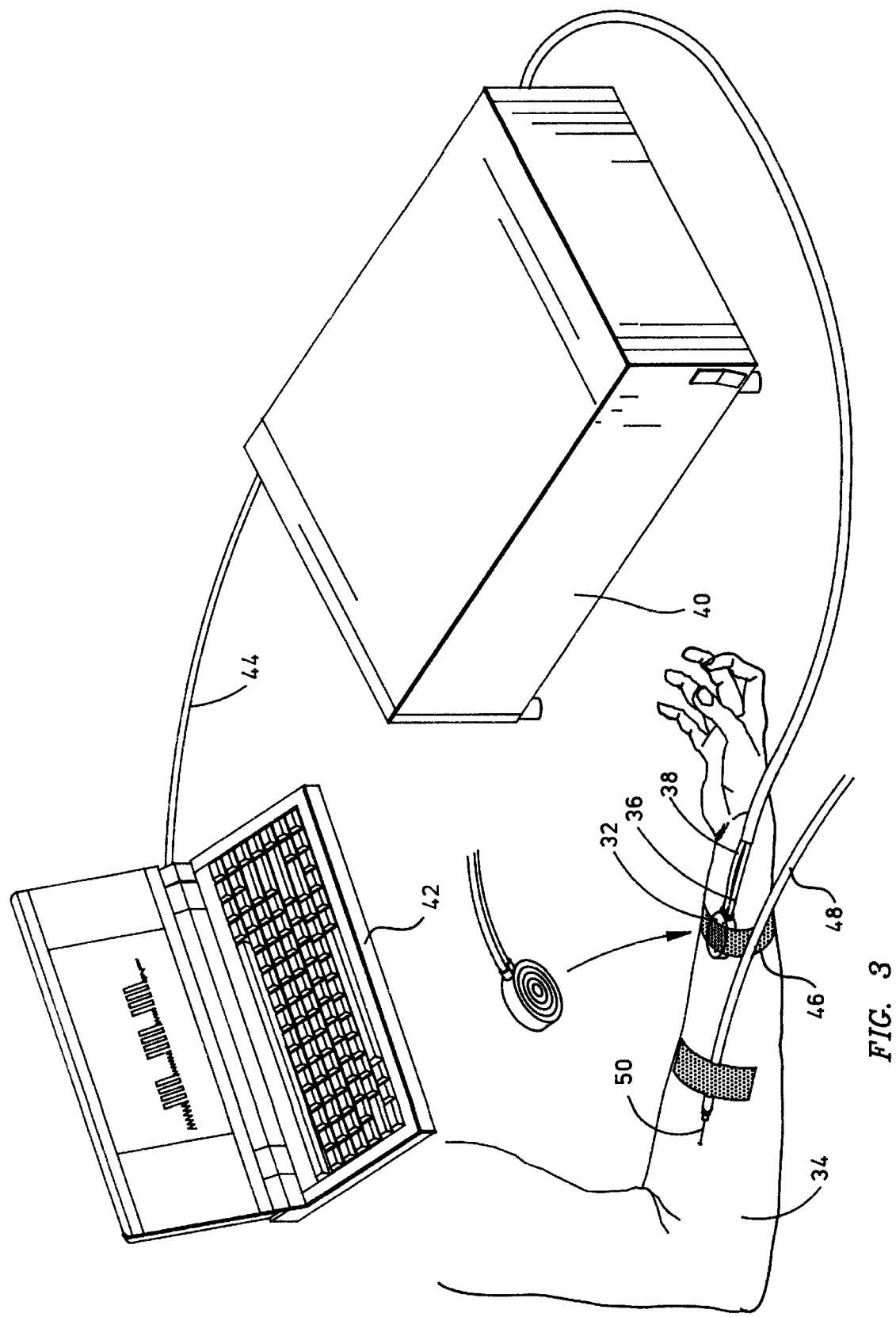
FIG. 3 is a perspective view of another embodiment of the apparatus for effecting in vivo electroporation of molecules into a blood vessel.

As used herein the term "molecules" includes pharmaceutical agents, genes, antibodies or other proteins. Referring to FIG. 1, an embodiment of the apparatus as disclosed in the grandparent application includes a device 12 which is implanted in a patient 10 for repeatedly generating electric fields of a predetermined amplitude and duration. This device embodies an induction coil and takes advantage of Faraday's law of electromagnetic induction to generate electric fields by induction. It is well known that the movement of a conductor through a magnetic field can induce an electric current in the conductor. A time varying electric current through a coil can generate a changing or time varying magnetic field which can also induce an electric field in the adjacent space, which in the present case is the underlying tissue and blood vessels. The induced electric field can be controlled by selecting the appropriate primary coil and its driving current. The fields are generated by applying a predetermined electric signal or current to the coil of the device.

The general law for the electric field associated with a changing magnetic field is:

$$\nabla \times E = -\frac{\partial B}{\partial t}$$

where: E=electric field, B=magnetic field, $\nabla \times E$ is the curl of the vector E and dB/dt is the time derivative of the magnetic field B.

This is called Faraday's law. This equation gives the "flux rule" for circuits.

Using Stokes' theorem, this law can be written in integral form as $$\oint_\Gamma E \cdot ds = \int_S (\nabla \times E) \cdot n\, da = -\int_S \frac{\partial B}{\partial t} \cdot n\, da$$

where, as usual $\Gamma$ is any closed curve and S is any surface bounded by it, ds os a dofferemtoa; line element s on the closed curve $\Gamma$, da is a differential area element a on the surface S, n is a unit vector (length 1) normal to the area element da, r is a specific resistivity and v is the velocity of either an electrical charge or a wire through which a current is flowing. A more thorough explanation of the electric field associated with a changing magnetic field and these equations can be found in American Institute of Physics Handbook, Second Edition, 1963, Page 5–40. See Also Handbook of Physics. Condon and Odishaw, McGraw-Hill, Second Edition, 1976, Page 1–136. $\Gamma$ is a mathematical curve fixed in space, and S is a fixed surface. Then the time derivative can be taken outside the integral and we have $$\text{INDUCED VOLTAGE} = \oint_\Gamma E \cdot ds = -\frac{\partial}{\partial t} \int_S B \cdot n\, da$$

$$= -\frac{\partial}{\partial t} (\text{flux through } S)$$

The integral on the left is the emf, and that on the right is the negative rate of change of the flux linked by the circuit.

So the "flux rule"—that the emf in a circuit is equal to the rate of change of the magnetic flux through the circuit—applies whether the flux changes because the field changes or because the circuit moves (or both). The two possibilities—"circuit moves" or "field changes"—are not distinguished in the statement of the rule. Yet these are two completely distinct laws for the two cases—v×B for "circuit moves" and $\nabla \times E = -\partial B/\partial t$ for "field changes".

In general, the force per unit charge is F/q=E+v×B. In moving wires there is the force from the second term. Also, there is an E-field if there is somewhere in changing magnetic field. They are independent effects, but the emf around the loop of a wire is always equal to the rate of change of magnetic flux through it.

The part of the emf that comes from the E-field does not depend on the existence of a physical wire (as does the v×B part). The E-field can exist in free space, and its line integral around any imaginary line fixed in space is the rate of change of the flux of B through that line. (Note that this is quite unlike the E-field produced by static charges, for in that case the line integral of E around a closed loop is always zero.)

The parameters of the signal are selected so that a quantity of blood flowing within the selected blood vessel is subjected to short pulses of high intensity electric fields. Typical electric field amplitudes required are several kV/cm at frequencies between 50 and 500 kH$_z$ for a duration of a few hundred microseconds or milliseconds. These fields make the walls of preselected cells in the blood transiently permeable to permit the molecules to enter said preselected cells without killing the cells. The permeability results from the temporary formation of pores in the cell walls which are large enough to permit migration of the molecules through the cell walls.

An exemplary embodiment of an implantable electric field generating device is illustrated in FIG. 2. In this implementation of the method, the electric field inside the blood vessel 14 is generated by an induction coil surrounding the blood vessel. As illustrated, a flexible single turn serpentine coil 16 surrounds the blood vessel 14. This coil is in the form of a serpentine coil 16 wound along a split dielectric cylinder 18 and having conductors 20 and 22 connected to a power pack 24. The device includes a fitting 26 for connection of a supply line or tube 28 from a supply pump 30. The supply line 28 may be provided with a spike tip as shown in FIG. 2a for communicating through the blood vessel. The dielectric cylinder can be expanded to be fit around the blood vessel 14. It may also be modified to extend around other external as well as internal parts of the body.

The function of the signal generator in the power pack 24 (FIG. 2) is to generate a predetermined repetitive electric current signal which, when applied to the coil 16 results in applying short bursts of oscillating electric fields of a predetermined amplitude and duration to the blood flowing through the blood vessel 14. Preferably these fields are applied repeatedly and their amplitude and duration are sufficient to make the walls of preselected cells in the blood sufficiently permeable to permit the molecules to enter the preselected cells without killing them.

Referring to FIG. 3, an alternate embodiment is illustrated wherein an external pancake induction coil 32 is applied directly to an arm 34 of a patient. The coil is positioned directly over a blood vessel (not shown) and connected by conductors 36 and 38 to a pulse power module 40 which provides repetitive current signals to the coil. The current to the coils is time varying and induces electric fields in the blood vessels. The power module is controlled by means of a computer 42 connected thereto by cable 44. The computer controls the repetitive rate of the power supply to be commensurate to the blood flow rate in the vessel. The coil may be secured in place by a strap or tape 46. Drugs or genes are infused via a tube 48 and needle 50 into the vein upstream of the coil so that is passes with the blood through the electric field.

This version can also be used for electroporation of other tissue of the body. The coil is placed closely adjacent the tissue to be electroporated and the appropriate electrical signal applied to achieve the desired electric field to produce electroporation of the tissue or cells of the tissue. The molecules to be introduced into the cells may be infused into the tissue by direct injection or by combinations of electroporation, iontophoresis and other means. This is particularly adaptable to the electroporation of tumors and the like. This approach eliminates the need for electrodes and possible conductivity problems sometimes associated with them.

Figure 4:
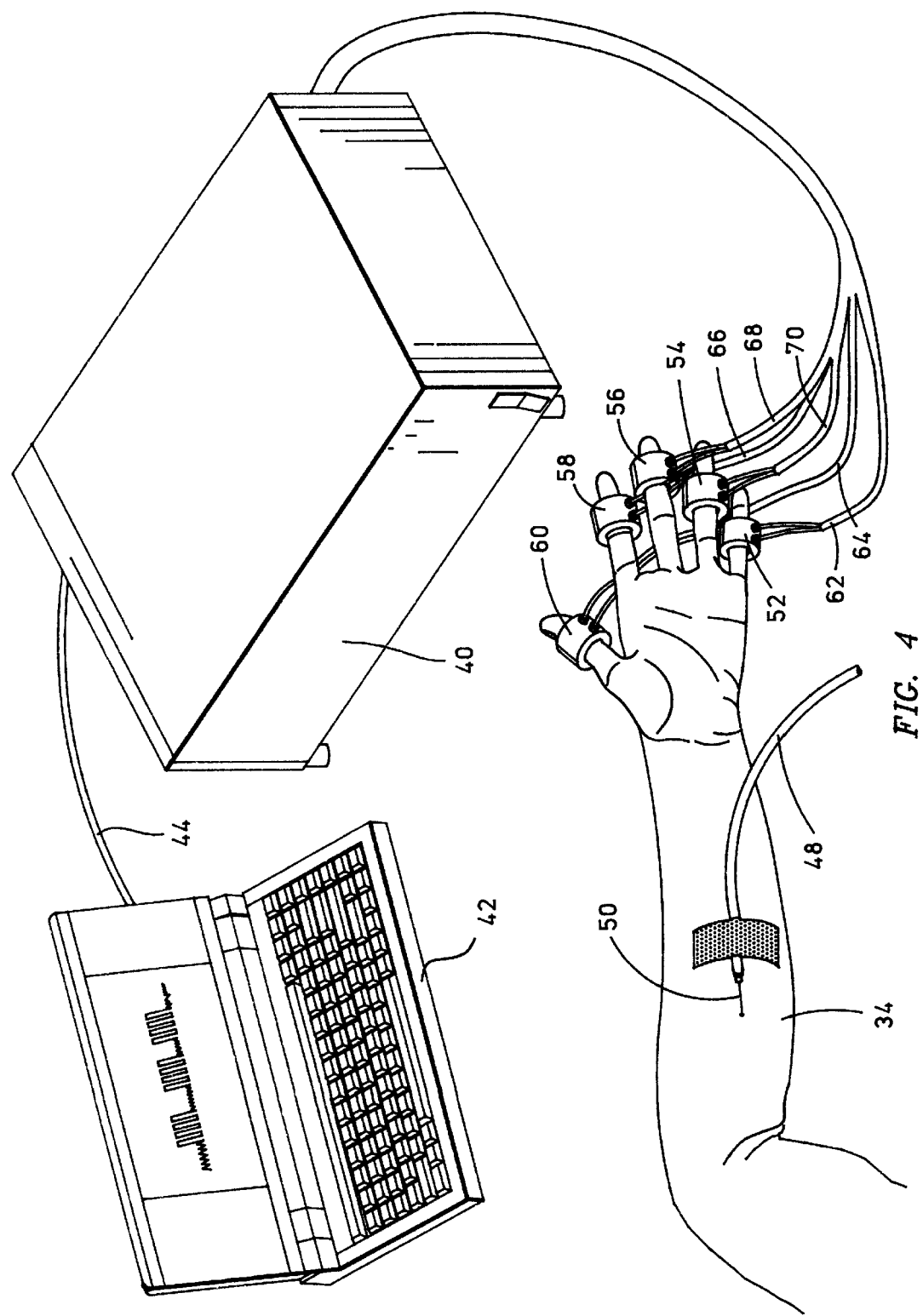
FIG. 4 is a perspective view of a further embodiment of the apparatus for effecting in vivo electroporation of molecules into a plurality of blood vessels.

Referring to FIG. 4, a further external embodiment is illustrated wherein like components are identified by the same reference numerals, a plurality of ring shaped induction coils 52, 54, 56, 58 and 60 are applied directly to the fingers of a patient. The coils are positioned on and encircle the fingers and are directly over a blood vessel (not shown) carrying blood to the ends of the fingers. The coils are connected by conductors 62, 64, 66, 68 and 70 to pulse power module 40 which provides repetitive current signals to the coil. The power module is controlled by means of a computer 42 connected thereto by a cable 44. The coil may be secured in place by a strap or tape (not shown). Drugs or genes are infused via a tube 48 and needle 50 into a vein upstream of the coils so that they flow through the electric field Alternative arrangements of this encircling embodiment may also be applied to a single finger or to other limbs or portions of the body. It may also be used to electroporate other tissue or cells of the body, both internally and externally. This induction coil approach provides a convenient means of electroporation of cells of internal organs without the need for physical invasion of the body.

The application of an electric field to the cell membrane results in the creation of transient pores which are critical to the electroporation process. Each cell species has its own critical fields strength for optimum electroporation. This is due to cell size, membrane makeup and individual characteristics of the cell wall itself. For example, some Gram positive bacteria are quite resistant to electroporation and require very high field strengths, i.e., greater than 17 kV/cm, before cell death and/or electroporation occurs.

By selecting the electrical parameters of the pulses, a preferred encapsulation into one of the different blood cell types is possible. If it is desirable to encapsulate drugs then one would preferably choose red blood cells as the target cells. If a gene is to be encapsulated, e.g., for gene therapy purposes, one would preferably choose white blood cells as target cells. The infused genes can then recombine with the genome of the white blood cells to alter their properties.

The preferred waveform of the electrical signal provided by the signal generator in the power pack 40 is a bipolar oscillating pulse train. The induced electric field strength can be from 0.2 kV/cm to 20 kV/cm. The pulse length can be from one microsecond to one hundred microseconds.

There can be one to one hundred pulses per liquid volume element as it passes through the blood vessel 20. Of course the waveform, electric field strength and pulse duration are dependent upon the type of cells and the type of molecules that are to enter the cells via electroporation. This induction coil approach to electroporation avoids the necessity of implanting electrodes inside a body for electroporation of cells deep inside the body. It also eliminates the problem of establishing a conductive path between the electrodes.

While there is described preferred embodiments of the electroporation method and apparatus for drug and gene delivery, it should be understood that modifications and adaptations thereof will occur to persons skilled in the art. For example, the power pack and pump could also be implanted inside the patient's body. Therefore, the protection afforded the invention should only be limited in accordance with the scope of the following claims.

I claim:

1. A method of in vivo introduction of molecules into living blood cells of a patient for therapeutic purposes, comprising the steps of:

providing an inductance device including an induction coil, the induction coil comprising at least one conductor having opposite ends adapted for connection to an electrical power source and at least one turn forming a coil intermediate the ends;

positioning said inductance device external of and closely adjacent to a body of the patient directly over a selected blood vessel for inducing an electric field at a preselected location within the selected blood vessel;

infusing preselected ones of said molecules into the selected blood vessel upstream of the inductance device; and applying time varying electric signals to the applied inductance device to generate time varying magnetic fields and repeatedly subject a quantity of blood flowing past the preselected location in the selected blood vessel to electric fields of a predetermined amplitude and duration, induced by the time varying magnetic fields, sufficient to make walls of preselected cells in said quantity of blood transiently permeable to permit the molecules to enter said preselected cells without killing said cells.

2. A method according to claim 1 wherein the molecules are selected from the group consisting of genes and pharmaceutical compounds.

3. A method according to claim 1 wherein the preselected cells are selected from the group consisting of red and white blood cells.

4. A method according to claim 1 wherein said induction coil surrounds a portion of the body containing the selected blood vessel.

5. A method according to claim 1 wherein the electric signals have a wave form comprising bipolar oscillating pulse train.

6. A method according to claim 5 wherein each pulse of the train has a duration of between approximately one microsecond and one hundred microseconds.

7. A method according to claim 5 wherein there are between approximately one pulse and one hundred pulses for a given unit of liquid volume as the unit passes through the selected blood vessel.

8. A method according to claim 1 wherein the electric fields have a strength of between approximately 0.2 kV/cm and 20.0 kV/cm.

9. A method according to claim 1 wherein the preselected cells are lymphocytes or red blood cells.

10. A method of in vivo introduction of molecules into living cells of a patient for therapeutic purposes, comprising the steps of:
   providing an inductance device including an induction coil, the induction coil comprising at least one conductor having opposite ends adapted for connection to an electrical power source and at least one turn forming a coil intermediate the ends;
   positioning said inductance device adjacent to an external portion of a body of the patient directly over a selected tissue for inducing an electric field at a preselected location within the selected tissue;
   infusing preselected ones of said molecules into the selected tissue; and
   applying a time varying electric signal to the applied inductance device to generate time varying magnetic fields and repeatedly subject tissue cells at the preselected location in the selected tissue to induce electric fields of a predetermined amplitude and duration sufficient to make the walls of preselected cells in the tissue transiently permeable to permit the molecules to enter said preselected cells without killing said cells.

11. A method according to claim 10 wherein the molecules are selected from the group consisting of genes and pharmaceutical compounds.

12. An apparatus for in vivo introduction of molecules into living blood cells of a patient, comprising:
   induction means including an induction coil comprising at least one conductor having opposite ends adapted for connection to an electrical power source and at least one turn forming a coil intermediate the ends, the coil adapted for positioning adjacent to an external portion of a body over and inducing an electric field at a preselected location within a blood vessel of the patient;
   means for injecting a predetermined quantity of a fluid medium carrying preselected ones of said molecules into the blood vessel up stream of the preselected location; and
   means for applying time varying electric signals to said induction coil for causing it to repeatedly generate magnetic fields and induce electric fields of a predetermined amplitude and duration sufficient to make walls of preselected cells in blood flowing past the preselected location in the blood vessel to be transiently permeable to permit the molecules to enter said preselected cells without killing said cells.

13. An apparatus according to claim 12 wherein the means for injecting the quantity of fluid carrying the molecules includes a pump.

14. An apparatus according to claim 12 wherein the means for applying electric signals includes a signal generator for generating the electric signals.

15. An apparatus according to claim 14 wherein the induction coil is a pancake coil for placing in contact with the patient over the blood vessel.

16. An apparatus according to claim 14 wherein the induction coils a ring shaped coil for placing around a finger of the patient.

17. An apparatus according to claim 16 wherein the induction coil is a plurality of ring shaped coils for placing around a plurality of the fingers of the patient.

18. An apparatus according to claim 12 wherein the induction coil is a pancake coil for placing in contact with the patient over the blood vessel.

19. An apparatus according to claim 12 wherein the induction coil is a ring-shaped coil for placing around a finger of the patient.

20. An apparatus according to claim 12 wherein the induction coil is a plurality of ring shaped coils for placing around a plurality of the fingers of the patient.

21. An apparatus according to claim 20 wherein the means for applying electric signals includes a signal generator to generating the electric signals.

* * * * *